United States Patent
Lai et al.

(10) Patent No.: US 7,315,645 B2
(45) Date of Patent: Jan. 1, 2008

(54) MEDIUM CATEGORY DETERMINATION METHOD FOR A MULTI-FUNCTION PERIPHERAL

(75) Inventors: Chung-Yi Lai, Taitung (TW); Chung-Yi Cheng, Taichung (TW)

(73) Assignee: Lite-On Technology Corporation, Taipei (TW)

( * ) Notice: Subject to any disclaimer, the term of this patent is extended or adjusted under 35 U.S.C. 154(b) by 787 days.

(21) Appl. No.: 10/671,523

(22) Filed: Sep. 29, 2003

(65) Prior Publication Data

US 2004/0190769 A1    Sep. 30, 2004

(30) Foreign Application Priority Data

Mar. 24, 2003    (TW) .............................. 92106544 A

(51) Int. Cl.
*G06K 9/00* (2006.01)
(52) U.S. Cl. ..................... 382/162; 382/165; 382/166; 382/167
(58) Field of Classification Search ............... 382/162, 382/165, 166, 167, 170; 356/326, 319; 430/506, 430/509
See application file for complete search history.

(56) References Cited

U.S. PATENT DOCUMENTS 5,314,794 A * 5/1994 Sutton ......................... 430/506
5,389,506 A * 2/1995 Sutton ......................... 430/509
7,075,643 B2 * 7/2006 Holub ......................... 356/326

FOREIGN PATENT DOCUMENTS

JP    2000333022    * 11/2000

* cited by examiner

*Primary Examiner*—Anh Hong Do
(74) *Attorney, Agent, or Firm*—Rabin & Berdo, P.C.

(57) ABSTRACT

A medium category determination method for a multi-function peripheral, which uses an algorithm to enhance the differences in the luminance values of three primary color and the corresponding standard deviations. The luminance values color and the corresponding standard deviations become precise bases for category determination of unknown media. Caused by the coarseness and the colors on the surfaces of different media, these differences under visible light are easily collected by scanning modules. The method scans the unknown medium to obtain the luminance values of three primary colors, calculates the corresponding standard deviations of all luminance values of the unknown medium, enhances the differences among the luminance values and standard deviations among the unknown medium and multiple known media by an algorithm, and finally determines the category of the unknown medium as the category of one known medium.

23 Claims, 5 Drawing Sheets
(3 of 5 Drawing Sheet(s) Filed in Color)

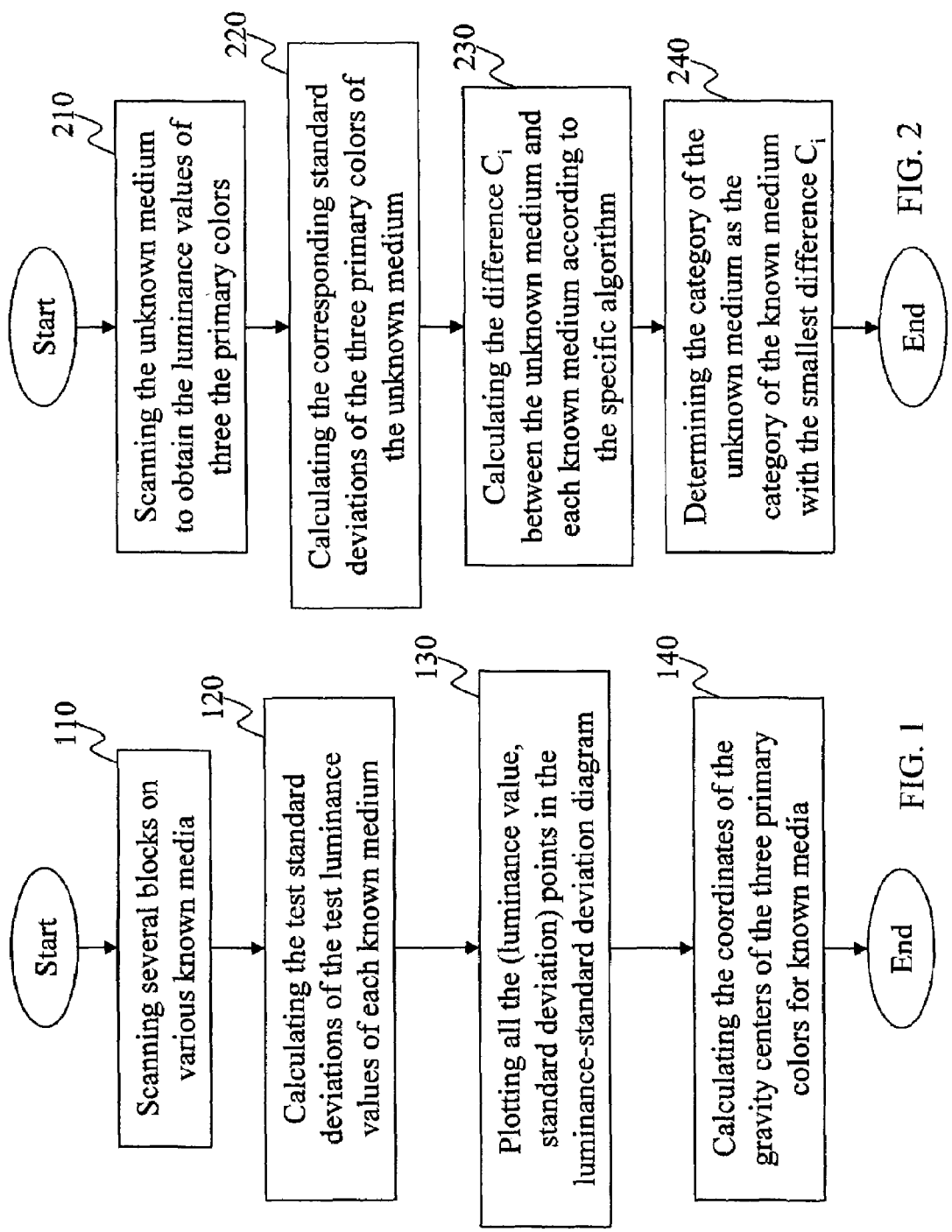

MEDIUM CATEGORY DETERMINATION METHOD FOR A MULTI-FUNCTION PERIPHERAL

FIELD OF THE INVENTION

The invention relates to a category determination method for printable media (papers), especially a determination method for a multi-function peripheral that enlarges the luminance differences of three primary colors between various media by executing a specific algorithm.

BACKGROUND OF THE INVENTION

"Downsizing" and "function integration" are the recent trends in developing information appliances. For a multi-function peripheral (referred to as an MFP), integrating printer, copier, fax and scanner functions not only means the combination and reorganization in physical structures, but also the merging and simplification of the functional related components under the requirement of downsizing.

A printer usually uses a paper sensor and a media sensor to determine the categories and the sizes of paper. Since the scan module has better sensing granularity and the capability to distinguish the scanned results of the three primary colors (i.e., red, green and blue), the paper and media sensors are replaced by the scan module in MFPs. Although scan modules can be used to determine the sizes and the categories of paper by the optical characteristics of scan modules, how to precisely determine the sizes and the categories of paper is still an important issue since there are various types of printable media including plain paper, transparencies and photo-paper. Because printing parameters are adjusted according to the category of paper, the determination results will affect the quality of printing. In addition, since the used paper determination method affects the precision of the determination, the quality of the used paper determination method is the key of the quality of printing.

One prior paper determination method is to print invisible ink codes which indicate the paper categories, manufacturers and some attributes on the paper. The advantage of this method is its high precision in determination. However, since the codes become visible when covered by ink, they are usually printed on the borders of the paper. As a result, the codes are visible in a full-bleed printing mode, and hence, the paper determination method is still problematic.

Another paper category determination method is to detect the diffuse reflectance and specular reflectance of paper with two sensors. The reflectance ratio of these two values is then compared with that of other known media stored in a database to determine the categories of paper. However, the precision of this method is not good enough because there are several media with the same reflectance ratio. As a result, printing parameters cannot be adjusted correctly.

Another paper category determination method utilized in the products of Hewlett-Packard Company is to obtain the reflectance factors by optical scanning, process these factors by Fourier transforming, and compare the frequency magnitude of the transformed signals to that of known media. Although this determination method avoids the problems mentioned above, the precision of determination is still not good enough since the frequency magnitude of the unknown medium is sometimes similar to that of known media in the database. This results from the competition of market, because of which an increasing number of media categories are produced with similar properties, and hence, the difficulty and error rate of determination is increased.

In addition, scan modules are capable of detecting the three primary colors, and hence can be used in paper determination in MFPs.

SUMMARY OF THE INVENTION

The object of the invention is to integrate the capability of detecting the three primary colors of scan modules and a difference enhancement algorithm of media properties to increase the precision of medium determination.

In view of the problems of the prior methods, the proposed determination method for a multi-function peripheral, used for determining the category of a medium, consists of the following steps. First, the unknown medium is scanned by a scan module of a multi-function peripheral in order to obtain the luminance values of the three primary colors, and the standard deviations of these luminance values are also calculated. Then, the luminance values and the corresponding standard deviations are compared with those of known media by a difference enhancement algorithm. Finally, the unknown medium is determined by a medium category determination execution module as the category of one of the known medium.

The effect of the invention is achieved by utilizing the luminance values of the three colors. The obtained luminance values and the corresponding standard deviations are more representative of the medium properties than any of the previously used single parameter. The proposed algorithm then enhances the differences of the medium properties to further increase the precision of the medium determination method.

BRIEF DESCRIPTION OF THE DRAWINGS

The application file contains at least one drawing executed in color. Copies of this patent application publication with color drawings will be provided by the Office upon request and payment of the necessary fee.

FIG. 1 is a flow chart showing the procedures to obtain the data of the known media;

FIG. 2 is a flow chart showing the determination method of the unknown medium category;

DETAILED DESCRIPTION OF THE PREFERRED EMBODIMENT

The proposed medium category determination method uses the differences in the luminance values and the corresponding standard deviations as a basis. The luminance variety is caused by the differences of the coarseness and the colors on the surfaces of media while illuminated by visible light. Collecting this information, enlarging the differences by the proposed algorithm, and then the differences are large enough to be precise bases for proceeding category determination. The method is described in detail by the following embodiments.

FIG. 1 shows the procedure to build the database of known media. The major object of the procedure is to obtain the "luminance samples" and "standard deviation samples". The procedure consists of the following steps.

First, provide a scan module to scan several blocks on various known media by the scan module (Step 110). Blocks on several known media are scanned to obtain the test luminance values of the three primary colors which consist of the test luminance values of red, green and blue. Possible scan modules to scan media include a charge-coupled device (CCD), contact image sensor (CIS), and so on. The known media in this example includes plain paper, photo-paper, coated-paper and transparencies.

Then, calculate the test standard deviations of the test luminance values of each known medium (Step 120). The corresponding standard deviations of the test luminance values of the three primary colors, called 'test standard deviations', are calculated. Standard deviation is an important parameter to evaluate variation in Statistics, and the consideration of standard deviation enables us to determine the differences between various media.

Figure 4:
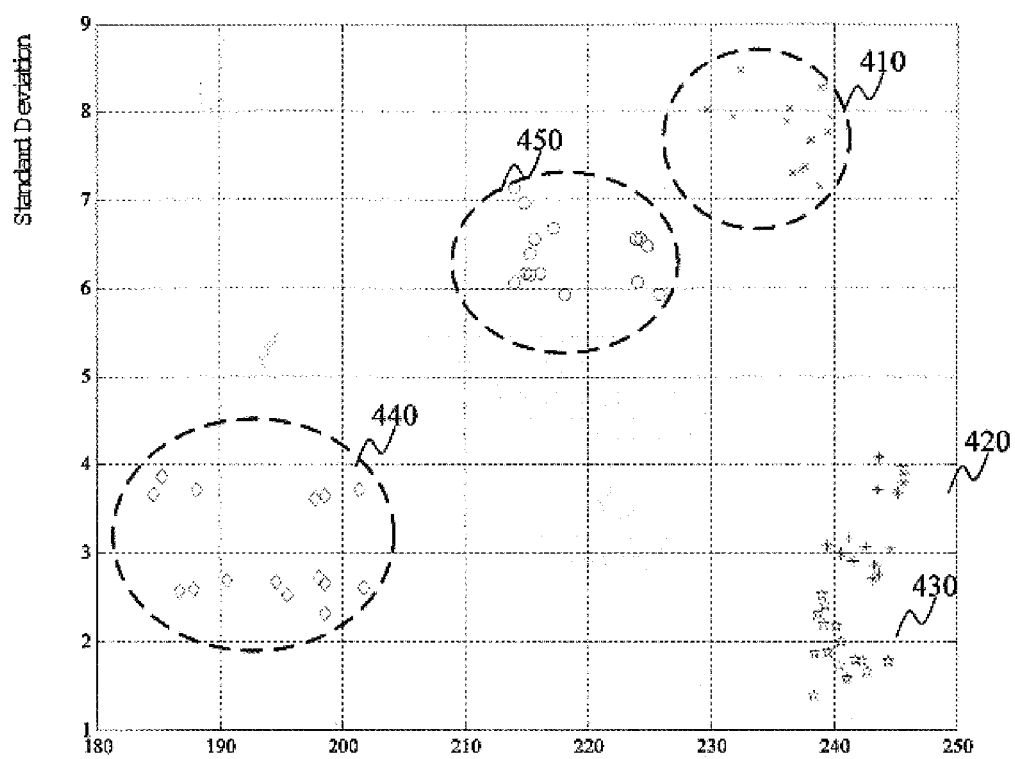
FIG. 4 is a luminance-standard deviation diagram showing the distribution of the scan results of several known media.

Next, plot all the (luminance value, standard deviation) points in the luminance-standard deviation diagram (Step 130). The test luminance values and the test standard derivations of the three primary colors of all known media are plotted in a luminance-standard deviation diagram. As shown in FIG. 4, area 410, 420, 430, 440 and 450 represent the test luminance values and standard deviations of the three primary colors of plain paper number two, coated-paper, photo-paper, transparency, and plain paper number one, respectively. It can be observed that the distributions of plain paper number one and two are very close. A similar situation occurs for coated and photo-paper.

Figure 5:
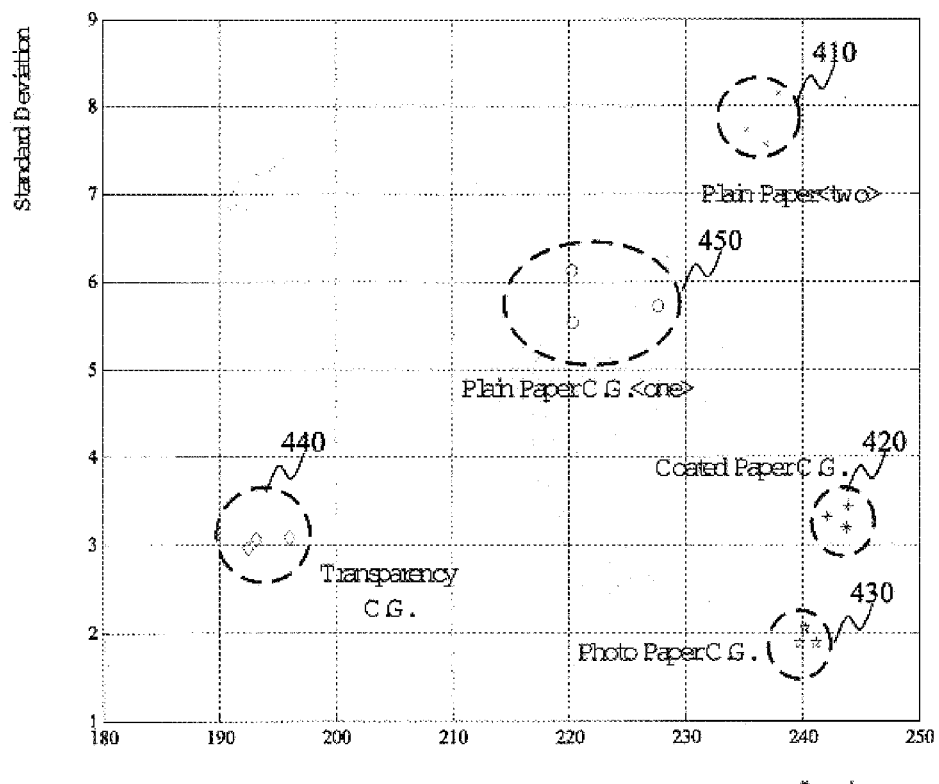
FIG. 5 is also luminance-standard deviation diagram, showing the distribution of the gravity centers of three primary colors of each known medium in FIG. 4.

In the end, calculate the coordinates of the gravity centers of the three primary colors for known media (Step 140). For each type of media, the centers of gravity of the luminance values of the three primary colors are calculated, and the coordinates of the centers of gravity are taken as the representative of each medium. As shown in FIG. 5, areas 410 and 450 are clearly separated. The same situation occurs for areas 420 and 430. The coordinates of the centers of gravity (luminance sample, standard deviation sample), are then taken as the bases of medium category determination.

Next, we use the following example to describe how to apply the proposed medium category determination method in an MFP. As shown in FIG. 2, scan the unknown medium to obtain the luminance values of three the primary colors by the scan module (Step 210). When an unknown medium is placed in the input panel of the MFP, the scan module starts scanning the unknown medium to obtain the luminance values of the three primary colors. The luminance values of the three primary colors consist of the luminance values of red, greed and blue. The scanned area is predetermined.

Calculate the corresponding standard deviations of the three primary colors of the unknown medium (Step 220). The standard deviations of the luminance values of the three primary colors are then calculated. The (luminance value, standard deviation) point for each primary color is plotted in a luminance-standard deviation diagram, and the results are shown in area 510 in FIG. 6.

Then, calculate the difference Ci between the unknown medium and each known medium according to the specific algorithm (Step 230). The difference between the unknown medium and each known medium is enhanced by the following algorithm. The difference between the unknown medium and a known medium is denoted as $C_i$, and $C_i$ can be formulated as:

$$C_i = w_r * d_{ri} + w_g * d_{gi} + w_b * w_{bi}, \text{ where}$$

i: the identification of the known medium, i=1~5;
$w_r$: the weighting of red;
$w_g$: the weighting of green;
$w_b$: the weighting of blue;
$d_{ri}$: the distance between the coordinates of red of the unknown medium and the i-th known medium in FIG. 6;
$d_{gi}$: the distance between the coordinates of green of the unknown medium and the i-th known medium in FIG. 6; and
$d_{bi}$: the distance between the coordinates of blue of the unknown medium and the i-th known medium in FIG. 6.

Finally, provide a medium category determination execution module to determine the category of the unknown medium as the category of the known medium with the smallest difference Ci (Step 240). The $C_i$ value for each known medium is checked, and the unknown medium is determined as the category of the known medium with the smallest $C_i$ value.

Figure 6:
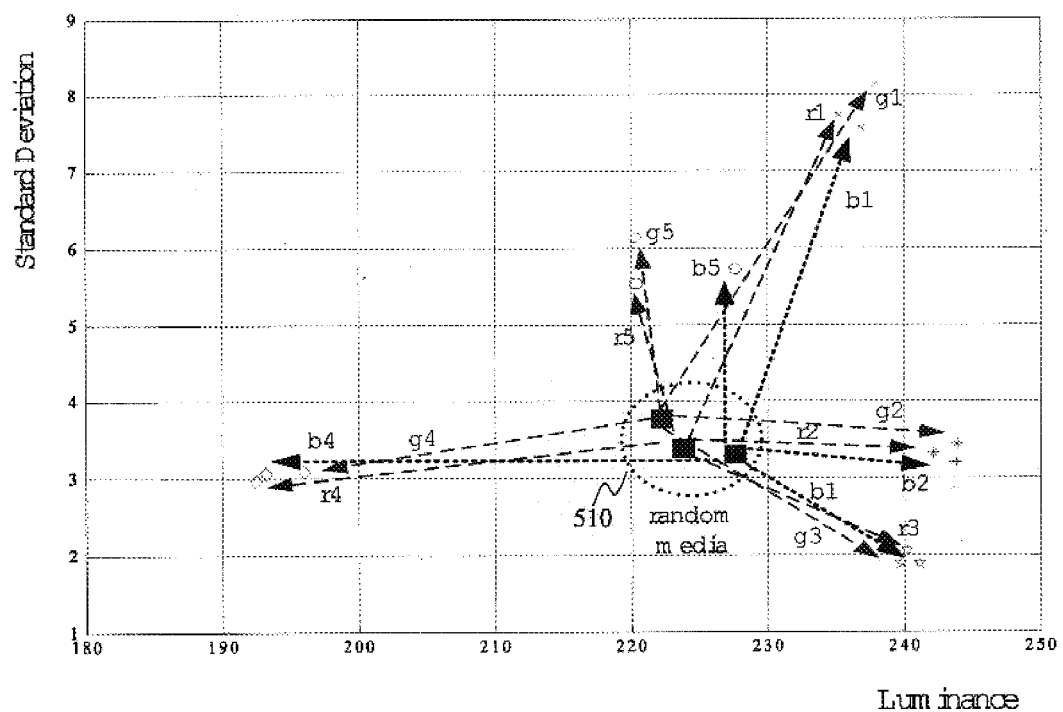
FIG. 6 is another luminance-standard deviation diagram, showing the relative positions among the centers of gravity of an unknown medium and each known medium in FIG. 5.

We can also collect the luminance values of several blocks of the unknown medium, and calculate the coordinates of the centers of gravity of the three primary colors. Hence, the three points of the unknown medium in the luminance-standard deviation diagram in FIG. 6 are more precise and the precision of the determination also increases.

Figure 3:
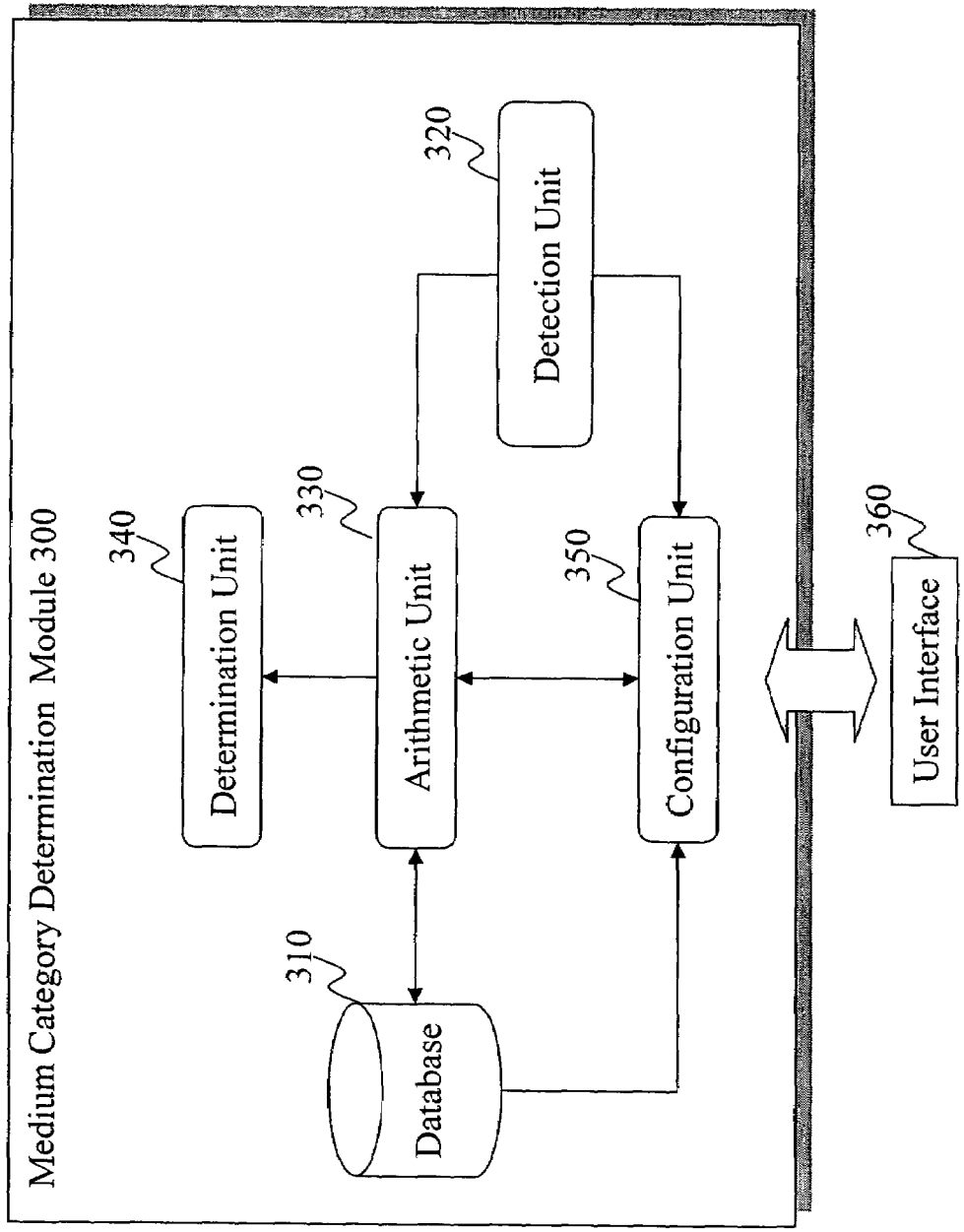
FIG. 3 is a system block diagram of the medium category determination module.

Although the concept of the invention is described with a luminance-standard deviation table, the proposed method can be implemented simply by arithmetic operations. A practical implementation of the proposed method requires a medium category determination execution module (300). As shown in FIG. 3, a medium category determination execution module consists of a database (310), a detection unit (320), an arithmetic unit (330), a determination unit (340) and a configuration unit (350). The functions of each unit are described below.

A database (310) is used to store the luminance samples and the corresponding standard deviation samples of known media, or the luminance-standard deviation diagrams. In essence, the MFP in this example has a set of printing parameters for each known medium stored in the database.

A detection unit (320) is used to control the scan module to scan an unknown medium and obtain the luminance values of the three primary colors of the unknown medium.

An arithmetic unit (330) is used to calculate the corresponding standard deviations after receiving the luminance values of the unknown medium from the detection unit (320). In addition, it retrieves the luminance samples and the standard deviation samples from the database (310), and calculates the difference $C_i$ for each known medium according to the proposed algorithm.

A determination unit (340) is used to determine the category of the unknown medium as the category of the known medium with the smallest difference $C_i$ on the basis of the results of the proposed algorithm.

A configuration unit (350) is used to generate a user interface (360) for users to manually determine the category of the medium or change the weights of the three primary colors in the proposed algorithm. The information provided by the user interface (360) includes the luminance values and the corresponding standard deviations of an unknown medium and a known medium, the weightings in the algorithm; the determination results of the unknown medium, and even the luminance-standard deviation diagram (such as FIG. 6) to show all (luminance, standard deviation) points for all known and unknown media.

The strength of the proposed medium category determination method is to collect all parameters of the three primary colors with one scan. When compared to a printer with single color detection capability, in the data collection phase, the invention uses more parameters to represent each medium. In addition, the invention provides a medium category determination mechanism with high precision by using the standard deviations and the difference enhancement algorithm.

While the preferred embodiment of the invention has been set forth for the purpose of disclosure, modifications of the disclosed embodiment of the invention as well as other embodiments thereof may occur to those skilled in the art. Accordingly, the appended claims are intended to cover all embodiments which do not depart from the spirit and scope of the invention.

What is claimed is:

1. A medium category determination method for determining the category of a medium in a multi-function peripheral, comprising the steps of:
    scanning an unknown medium to obtain a luminance value of red, a luminance value of green and a luminance value of blue using a scan module;
    calculating the corresponding standard deviations of said luminance values of the unknown medium;
    applying an algorithm on the luminance values and the standard deviations of the unknown medium, and on a plurality of luminance samples and corresponding standard deviation samples from a plurality of known media; and
    applying a result of the application of said algorithm to determine the category of the unknown medium as the category of one of the known media, using a medium category determination execution module.

2. The method according to claim 1, wherein the algorithm determines the category of the unknown medium as the category of the known medium with the smallest $C_i$, which is defined as $C_i = w_r * d_{ri} + w_g * d_{gi} + w_b * w_{bi}$, where
    i: the identification of the known medium;
    $w_r$: the weighting of red;
    $w_g$: the weighting of green;
    $w_b$: the weighting of blue;
    $d_{ri}$: the distance between the coordinates of red of the unknown medium and the i-th known medium in a luminance-standard deviation coordinate system;
    $d_{gi}$: the distance between the coordinates of green of the unknown medium and the i-th known medium in the luminance-standard deviation coordinate system; and
    $d_{bi}$: the distance between the coordinates of blue of the unknown medium and the i-th known medium in the luminance-standard deviation coordinate system.

3. The method according to claim 2, wherein the luminance samples and the standard deviation samples are provided by the steps of:
    scanning a plurality of blocks on the known medium to obtain a plurality of test luminance values of red, green and blue;
    calculating the test standard deviations of the test luminance values of the known medium;
    calculating the coordinates of the gravity centers of the test luminance values and the test standard deviations of red, green and blue in the luminance-standard deviation coordinate system, and taking the coordinates of the gravity centers as the representatives of the known medium.

4. The method according to claim 2, which is executed by a medium category determination module comprising:
    a database storing the luminance samples and the standard deviation samples of the known media;
    a detection unit controlling a scan module to scan the unknown medium to obtain the luminance values of red, green and blue;
    an arithmetic unit which receives the luminance values of the unknown medium from the detection unit, calculates the corresponding standard deviations, retrieves the luminance samples and the standard deviation samples from the database, and calculates the $C_i$s for the known medium according the algorithm; and
    a determination unit determining the category of the unknown medium as the category of one of the known media with the smallest $C_i$.

5. The method according to claim 4, wherein the medium category determination module further comprises a configuration unit to generate a user interface for users to determine the categories of the unknown media.

6. The method according to claim 5, wherein the configuration unit enables users to change the weightings of the algorithm.

7. The method according to claim 5, wherein the configuration unit further provides a luminance-standard deviation diagram to show the distribution of (luminance value, standard deviation) points of the known media and the unknown medium.

8. The method according to claim 1, wherein the known media are selected from the group consisting of plain paper, photo-paper, coated-paper and transparency.

9. The method according to claim 1, wherein the scan of the unknown medium is done by a scan module.

10. The method according to claim 9, wherein the scan module is a charge-coupled device (COD) or a contact image sensor (CIS).

11. The method according to claim 1, further comprising the step of printing on the unknown medium based on the determined category.

12. A medium category determination method for determining the category of a medium, comprising the steps of:
    scanning an unknown medium to obtain a luminance value of red, a luminance value of green and a luminance value of blue using a scan module;
    calculating the corresponding standard deviations of said luminance values of the unknown medium; and
    applying an algorithm on the luminance values and the standard deviations of the unknown medium, and on a plurality of luminance samples and corresponding standard deviation samples from a plurality of known media; and
    applying a result of the application of said algorithm to determine the category of the unknown medium as the category of one of the known media, using a medium category determination execution module;
    wherein the algorithm determines the category of the unknown medium as the category of the known medium with the smallest $C_i$, which is defined as $C_i = w_r * d_{ri} + w_g * d_{gi} w_b * w_{bi}$, where
    i: the identification of the known medium;
    $w_r$: the weighting of red;
    $w_g$: the weighting of green;
    $w_b$: the weighting of blue;
    $d_{ri}$: the distance between the coordinates of red of the unknown medium and the i-th known medium in a luminance-standard deviation coordinate system;
    $d_{gi}$: the distance between the coordinates of green of the unknown medium and the i-th known medium in the luminance-standard deviation coordinate system; and
    $d_{bi}$: the distance between the coordinates of blue of the unknown medium and the i-th known medium in the luminance-standard deviation coordinate system.

13. The method according to claim 12, wherein the luminance samples and the standard deviation samples are provided by the steps of:

scanning a plurality of blocks on the known medium to obtain a plurality of test luminance values of red, green and blue;

calculating the test standard deviations of the test luminance values of the known medium;

calculating the coordinates of the gravity centers of the test luminance values and the test standard deviations of red, green and blue in the luminance-standard deviation coordinate system, and taking the coordinates of the gravity centers as the representatives of the known medium.

14. The method according to claim 12, wherein the method is executed by a medium category determination module, which comprises:

a database storing the luminance samples and the standard deviation samples of the known media;

a detection unit controlling a scan module to scan the unknown medium to obtain the luminance values of red, green and blue;

an arithmetic unit which receives the luminance values of the unknown medium from the detection unit, calculates the corresponding standard deviations, retrieves the luminance samples and the standard deviation samples from the database, and calculates the $C_i$s for the known medium according the algorithm; and a determination unit determining the category of the unknown medium as the category of one of the known media with the smallest $C_i$.

15. The method according to claim 14, wherein the medium category determination module further comprises a configuration unit to generate a user interface for user to determine the category of the unknown medium.

16. The method according to claim 15, wherein the configuration unit enables users to change the weightings of the algorithm.

17. The method according to claim 15, wherein the configuration unit provides a luminance-standard deviation diagram to show the distribution of the (luminance value, standard deviation) points of the known media and the unknown medium.

18. The method according to claim 12, wherein the known media are selected from the group consisting of plain paper, photo-paper, coated-paper and transparency.

19. The method according to claim 12, wherein the unknown medium is scanned by a scan module.

20. The method according to claim 19, wherein the scan module is a charge-coupled device (CCD) or a contact image sensor (CIS).

21. The method according to claim 19, wherein the scan module is placed in a MFP.

22. The method according to claim 12, further comprising the step of printing on the unknown medium based on the determined category.

23. A medium category determination method, comprising the steps of:

scanning an unknown medium to obtain a luminance value of red, a luminance value of green and a luminance value of blue;

calculating the corresponding standard deviations of said luminance values of the unknown medium;

applying an algorithm on the luminance values and the standard deviations of the unknown medium, and on a plurality of luminance samples and corresponding standard deviation samples from a plurality of known media;

applying a result of the application of said algorithm to determine the category of the unknown medium as the category of one of the known media; and printing on the unknown medium based on the determined category.

* * * * *